United States Patent
Atsumi et al.

(10) Patent No.: US 7,244,574 B2
(45) Date of Patent: Jul. 17, 2007

(54) METHOD OF ASSAYING LUPUS ANTICOAGULANT AND ASSAY REAGENT

(75) Inventors: Tatsuya Atsumi, Sapporo (JP); Takao Koike, Sapporo (JP)

(73) Assignee: Eisai Co., Ltd, Tokyo (JP)

( * ) Notice: Subject to any disclaimer, the term of this patent is extended or adjusted under 35 U.S.C. 154(b) by 455 days.

(21) Appl. No.: 10/472,283

(22) PCT Filed: Mar. 19, 2002

(86) PCT No.: PCT/JP02/02599

§ 371 (c)(1),
(2), (4) Date: Sep. 18, 2003

(87) PCT Pub. No.: WO02/074972

PCT Pub. Date: Sep. 26, 2002

(65) Prior Publication Data

US 2004/0110242 A1    Jun. 10, 2004

(30) Foreign Application Priority Data

Mar. 19, 2001    (JP) .............................. 2001-077366

(51) Int. Cl.
*G01N 33/05* (2006.01)
(52) U.S. Cl. ...................... 435/7.1; 435/7.2; 435/7.92; 530/387.1; 530/387.7; 530/388.2
(58) Field of Classification Search ............. 530/387.1, 530/387.7, 388.2; 435/7.1, 7.2, 7.92
See application file for complete search history.

(56) References Cited

FOREIGN PATENT DOCUMENTS

WO    WO 00/02925    1/2000

OTHER PUBLICATIONS

Galil et al. Thrombosis and Haemostasis 1999 vol. 77, p. 486-91.*
Atsumi, et al., "Association of Autoantibodies Against the Phosphatidylserine-Prothrombin Complex with Manifestations of the Antiphospholipid Syndrome and with the Presence of Lupus Anticoagulant", *Arthritis & Rheumatism*, 43(9): 1982-1993, 2000.
Atsumi, et al., "Anti Prothrombin-Phosphatidylserine Antibodies and Their Association with Lupus Anticoagulant in Japanese Patients with Autoimmune Diseases", Abstract. No. B077.
Atsumi, et al., "Characteristics of Phosphatidylserine-Dependent Mouse Monoclonal Antiprothrombin Antibodies", Abstract. No. P32.
Atsumi, et al., "Clinical Significance of Anti Prothrombin-Phosphatidylserine Antibodies and Their Association with Lupus Anticoagulant in Patients with Autoimmune Diseases", Abstract. No. 821.
Journal of Autoimmunity, vol. 15, No. 2, Sep. 2000, p. A38, XP009033955 9th International Symposium on Antiphospholipid Antibodies; Tours, France; Sep. 12-16, 2000 ISSN 0896-8411.
"A Monoclonal Antibody Against Prothrombin Fragment 1 Behaves Like a Lupus Anticoagulant," Thombosis and Haemostasis, Stuttgart, DE, 81(3): Mar. 1999, 470-471.
Matsuda et al., "Phosphatidyl Serine-Dependent Antiprothrombin Antibody is Exclusive to Patients with Lupus Anticoagulant," *British Journal of Rheumatology*,35(6): 589-591, 1996.
International Search Report for EP 02 70 5339.

* cited by examiner

*Primary Examiner*—Long V. Le
*Assistant Examiner*—Jacob Cheu
(74) *Attorney, Agent, or Firm*—Andrea L. C. Robidoux; Choate, Hall & Stewart

(57) ABSTRACT

A monoclonal antibody having inhibitory activity on blood coagulation reactions, which reacts with prothrombin forming a complex with phosphatidylserine but does not react with prothrombin not forming a complex with phosphatidylserine; and a method for measuring inhibitory activity of test plasma on blood coagulation reactions, which comprises the steps of (1) measuring inhibitory activity of the test plasma on the blood coagulation reactions and inhibitory activity of this on the blood coagulation reactions, and (2) comparing the inhibitory activity of the test plasma with the inhibitory activity of this antibody.

5 Claims, 2 Drawing Sheets

METHOD OF ASSAYING LUPUS ANTICOAGULANT AND ASSAY REAGENT

TECHNICAL FIELD

The present invention relates to a method and a reagent for measuring lupus anticoagulant (referred to as LA hereinafter), which appears concomitantly with antiphospholipid antibody syndrome.

BACKGROUND ART

The antiphospholipid antibody syndrome (referred to as APS hereinafter) is an autoimmune disease with clinical manifestations including arterial or venous thrombosis, abortion and stillbirth, in which autoantibodies called antiphospholipid antibodies are identified in blood. According to the definition of APS, identification of antiphospholipid antibodies (referred to as aPL hereinafter) is essential for diagnosis. However, aPLs constitute an extremely diverse autoantibody group, and detection of them is not necessarily easy. Draft of amended APS classification criteria was prepared in 1999, and the draft included the following descriptions regarding test items:

1) moderate or higher level of IgG or IgM-type $\beta_2$ glycoprotein I-dependent anticardiolipin antibodies; and 2) positive result for LA However, it is said that the LA test is one of the most difficult tests for both of clinicians and clinical technologists, and it is known that results thereof vary to a large extent depending on test methods, reagent types and specimen conditions.

LA is defined as "immunoglobulins that inhibit in-vitro phospholipid-dependent coagulation reactions (reactions for activated partial thromboplastin time (Triplett LA. Lupus 7 (Supple. 2), S18-22, 1998; also referred to as aPTT hereinafter), kaolin clotting time (Triplett LA. Lupus 7 (Supple. 2), S18-22, 1998; also referred to as KCT hereinafter) and dilute Russell's viper venom time (Triplett LA. Lupus 7 (Supple. 2), S1B-22, 1998; also referred to as dRVVT hereinafter))", and the Committee for Antiphospholipid Antibody standardization of Xnternational Society on Thrombosis and Hemostasis provided guidelines of testing in 1995.

Various means have been devised in each institution to increase sensitivity and specificity. However, it is still difficult to determine the presence of LA by a single method, and several methods are usually employed in combination for the determination. That is, these are used the steps of:

1) screening for prolongation of the phospholipid-dependent coagulation time with aPTT, KCT and dRVVT;

2) demonstrating that this prolongation of the coagulation time is resulted from the presence of an inhibitor in plasma of patient by the mixing test (addition of normal plasma); and 3) confirming that this inhibitor is an antiphospholipid antibody by an absorption and neutralization test using impaired platelets or phospholipid.

Since LA inhibits phospholipid-dependent reactions, reduction of the phospholipid concentration is required for highly sensitive detection of LA. However, even under such a condition, selection and preparation of reagents and determination of standard values need to be done in each institution, and thus there is a problem that results still vary to a large extent among institutions. Accordingly, quantitative LA assay is not generally conducted.

Regarding an index associated with LA, Atsuni T et al., Arthritis Rheum 43: 1982-93, 2000 reported that a phosphatidylserine-dependent antiprothrombin antibody (referred to as aPS/PT hereinafter), which reacts only with prothrombin forming a complex with phosphatidylserine in blood of a patient (also referred to as PS/PT hereinafter), closely correlates with LA. However, relation of antibodies directed to blood coagulation factor/phospholipid complexes other than aPS/PT to LA cannot be ruled out. Thus, it remains unknown whether a monoclonal antibody that does not bind to these complexes, aPT/PS, inhibits blood coagulation or can be used as a standard for LA.

DISCLOSURE OF THE INVENTION

An object of the present invention is to enable precise measurement of LA, which has conventionally provided a large difference among institutions, by establishing a semi-quantitative LA measurement method using antibodies serving as a standard.

The inventors of the present invention hypothesized that inhibitory activity against blood coagulation in patient's serum containing autoantibodies directed to diverse blood coagulation factor/phospholipid complexes could be measured by using monoclonal aPS/PT as a representative, and considered that, if mouse monoclonal aPS/PT was produced and used as a standard to measure the coagulation activity, the measurements of LA, which had provided large differences among institutions, might be performed with good precision. Then, the inventors of the present invention successfully produced mouse monoclonal aPS/PT that did not react with prothrombin (also referred to as PT hereinafter) but reacted only with PS/PT, and revealed that this monoclonal antibody inhibited blood coagulation reactions and could be used as a standard antibody in the LA measurement, and further revealed that LA could be precisely and semi-quantitatively measured by using this monoclonal antibody as a standard.

The inventors of the present invention designated the produced hybridoma as 231D cells and the produced antibody as 231D antibody.

The present invention thus provides the followings:

1. A monoclonal antibody having inhibitory activity on blood coagulation reactions, which reacts with prothrombin forming a complex with phosphatidylserine but does not react with prothrombin not forming a complex with phosphatidylserine.

2. The monoclonal antibody according to 1, wherein the monoclonal antibody is derived from a mouse.

3. The monoclonal antibody according to 1, wherein the monoclonal antibody is an antibody produced by 231D cells (FERM BP-7936).

4. A method for measuring inhibitory activity of test plasma on blood coagulation reactions, which comprises the steps of:

(1) measuring inhibitory activity of the test plasma on the blood coagulation reactions and inhibitory activity of the antibody as defined in any one of 1 to 3 on the blood coagulation reactions; and (2) comparing the inhibitory activity of the test plasma with the inhibitory activity of the antibody as defined in any one of 1 to 3.

5. A method for measuring lupus anticoagulant in test plasma, which comprises steps of measuring inhibitory activity by the method as defined in 4 and determining a lupus anticoagulant level by using the inhibitory activity as an index.

6. The method according to 4, wherein the method for measuring the inhibitory activity on blood coagulation reactions is any of measurement of prolongation of activated partial thromboplastin time, measurement of prolongation of kaolin clotting time, and measurement of prolongation of dilute Russell's viper venom time, or a combination thereof.

7. A reagent for measuring lupus anticoagulant, which contains the monoclonal antibody as defined in any one of 1 to 3 as a constitutive reagent.

8. A method for producing the monoclonal antibody as defined in 1 or 2, which comprises collecting monoclonal antibodies produced by an antibody-producing cell selected by a selection method comprising the steps of;

(1) selecting an antibody-producing cell producing a monoclonal antibody that reacts with prothrombin forming a complex with phosphatidylserine, and (2) further selecting an antibody-producing cell producing a monoclonal antibody that does not react with prothrombin not forming a complex with phosphatidylserine.

BEST MODE FOR CARRYING OUT THE INVENTION

Figure 1:
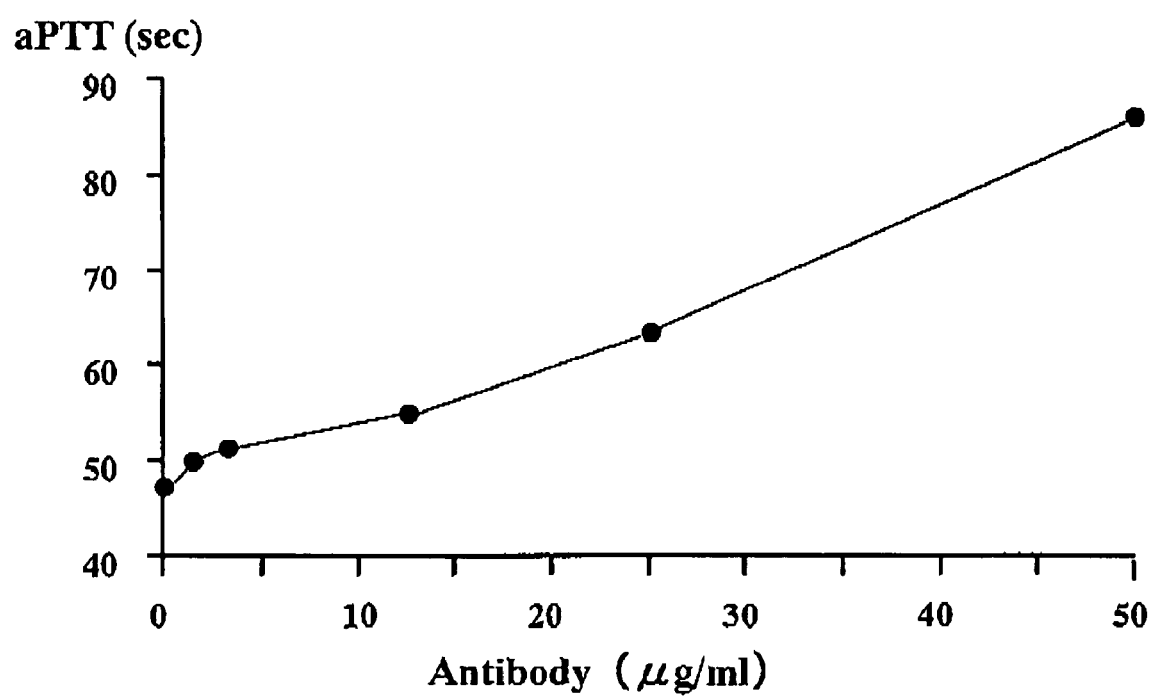
FIG. 1 shows a standard curve of coagulation time for aPTT obtained by using the 231D antibody as a standard.

The antibody of the present invention is a monoclonal antibody that reacts with prothrombin forming a complex with phosphatidylserine (PS/PT) but does not react with prothrombin (PT) not forming a complex with phosphatidylserine, and has inhibitory activity on blood coagulation reactions.

In the present invention, the expression "antibody reacts" means that it reacts immunologically. Further, the complex of phosphatidylserine (PS) and prothrombin (PT) means a complex formed by PS and PT under a condition close to the physiological condition (for example, pH 7.5, PS:PS=3:1 (weight ratio)). The inhibitory activity on blood coagulation reactions can be measured based on change in a value used as an index of the blood coagulation reactions when the monoclonal antibody exists in a reaction system. Examples of such a value include aPTT, dRVVT, KCT and so forth.

The monoclonal antibody of the present invention is preferably derived from a mouse.

The monoclonal antibody of the present invention is produced by collecting lymphocytes from an animal immunized with human prothrombin (the origin may also be a human having autoantibodies directed to human prothrombin), immortalizing them, then selecting a clone (antibody-producing cell) producing antibodies that reacts with PS/PT but not with PT and collecting antibodies produced by the clone.

The immortalization method is not particularly limited. Immortalization can be performed by a method of infecting with virus (EBV for human cells), a method of fusing cells or the like.

The method for selecting a antibody-producing cell is not particularly limited so long as an antibody that reacts with PS/PT but not with PT is selected. However, the antibody-producing cell is preferably selected by a selection method comprising the steps of:

(1) selecting an antibody-producing cell producing a monoclonal antibody that reacts with PS/PT; and (2) further selecting an antibody-producing cell producing a monoclonal antibody that does not reacts with PT.

Although antibodies that react with PS/PT but not with PT usually have inhibitory activity on blood coagulation reactions, it may be confirmed as required.

The method for collecting the antibody produced by the antibody-producing cell is not particularly limited, either. The monoclonal antibody can be produced by a method based on cell culture, a method based on production of antibodies in ascites of mouse or the like, and produced monoclonal antibody can be purified by a method conventionally used in purification of antibodies.

Hereafter, the method for producing mouse monoclonal aPS/PT will be specifically described as an example. However, the scope of the present invention is not limited to this example.

If necessary, purified or partially purified human prothrombin or human plasma is subjected to a suitable treatment for increasing immunogenicity, for example, a treatment of preparing emulsion together with Freund's complete adjuvant or Freund's incomplete adjuvant or the like, and then administered to the mouse subcutis, peritoneal cavity, footpad or the like to attain immunization. If necessary, immunization is repeated two or more times at appropriate intervals.

An organ containing antibody-producing cells such as spleen or lymph node is removed from the immunized mouse, and lymphocytes are passed through a mesh to separate them. The separated lymphocytes are fused with myeloma cells such as P3U1 cells by the following method. However, the method for the cell fusion is not limited to this method.

Lymphocytes and P3U1 cells are washed twice with RPMI-1640 medium, mixed at a ratio of 5:1 to 10:1, suspended in RPMI-1640 medium and centrifuged at 1500 rpm for 5 minutes. After cell aggregation is loosened, 1 ml of 50% PEG solution (Boehringer) warmed at 37° C. beforehand is gradually added over 2 minutes and successively 20 ml of RPMI-1640 medium warmed at 37° C. beforehand is gradually added with 3 minutes. The mixture is centrifuged at 1000 rpm for 5 minutes and then left for 5 minutes.

Supernatant is removed, and then the lymphocyte cells are suspended in 10% FCS/RPMI-1640 medium at $1 \times 10^6$ cells/ml and introduced into wells of a 96-well plate in a volume of 100 μl per well. On the following day, 100 μl per well of 10% FCS/2× HAT (Lifetech)/RPMI-1640 medium is added to perform HAT selection of hybridoma and thereby select fused cells. In order to promote the growth of hybridomas, the cells are preferably cultured with thymus cells of a syngeneic mouse or cultured with addition of, for example, a 1/10 amount of ORIGEN HCF (ICGS). The culture is continued for an appropriate number of days, preferably 1 to 2 weeks, and the culture supernatant is used for assay of antibodies.

A clone producing an antibody that reacts with PS/PT but not with PT is selected from the obtained clones. Although the reaction with PS/PT or PT may be performed in a liquid phase, the reaction performed in a solid phase will be explained below, of which procedure is easier.

First, a method of forming PS/PT on a solid phase and identifying a clone that reacts with PS/PT will be described. Phosphatidylserine is dissolved in a solvent, for example, methanol/chloroform, at a suitable concentration, for example, 50 µg/ml, and placed on an ELISA plate (Sumitomo Bakelite), and then the solvent is evaporated. Then, in order to prevent antibodies from non-specifically adsorbing on the ELISA plate, a buffer (blocking solution) containing a protein such as albumin, casein (skim milk) or gelatin and $Ca^{2+}$ at a suitable concentration, for example, 5 mM, is added to the ELISA plate to perform blocking.

After washing, a prothrombin solution obtained by adding human prothrombin to the blocking solution at a suitable concentration, for example, 10 µg/ml, is added to the ELISA plate. The added human prothrombin is bound to phosphatidylserine via the gla region in the presence of $Ca^{2+}$, and thus PS/PT is formed with a changed three-dimensional structure. As a control, a well to which the blocking solution not containing human prothrombin is added is also prepared.

The collected hybridoma culture supernatant is added to the ELISA plate on which PS/PT is formed and reacted. After washing, an anti-mouse Ig antibody suitably labeled, for example, with an enzyme such as alkaline phosphatase or peroxidase, a fluorescent substance or a radioactive substance are added and reacted. After washing, measurement is performed by a method according to the label. For example, when an enzyme label is used, an enzyme substrate is added to obtain coloration, when a fluorescent label is used, fluoresc nce intensity is measured, and when a radioactive label is used, radioactivity is measured. Among the clones in the wells containing human prothrombin, clones in wells in which the label is more intensely observed compared with wells not containing human prothrombin are identified as clones producing antibodies that react with PS/PT.

The buffer used for the washing preferably contains $Ca^{2+}$ at a suitable concentration, for example, 5 mM, as well as a suitable surfactant, for example, 0.05% Tween 20.

Hereafter, a method for selecting a clone producing an antibody that does not react with PT will be explained. Human prothrombin is added to an ELISA plate at a suitable concentration, for example, 10 µg/ml. After washing, in order to prevent antibodies from non-specifically adsorbing on the ELISA plate, a buffer containing a protein such as albumin, casein (skim milk) or gelatin is added to the ELISA plate to perform blocking.

Culture supernatant of hybridoma that reacts with PS/PT is added to the ELISA plate and reacted. After washing, an anti-mouse Ig antibody suitably labeled, for example, with an enzyme such as alkaline phosphatase or peroxidase, a fluorescent substance or a radioactive substance are added and reacted. After washing, measurement is performed by a method according to the label. For example, when an enzyme label is used, an enzyme substrate is added to obtain coloration, when a fluorescent label is used, fluorescence intensity is measured, and when a radioactive label is used, radioactivity is measured. Clones in wells in which the label is not observed are identified as clones producing antibodies that do not react with PS/PT.

The aforementioned immunization of mammal, acquisition of antiserum, production of hybridoma and enzyme-labeled antibody technique can be performed according to methods described in references, for example, Ed Harlow, David Lane, Antibodies A Laboratory Manual, Cold Spring Harbor Laboratory (1988).

An antibody is purified from supernatant of the culture in which the obtained clone cells are cultured or ascite of mouse to which the clone cells are inoculated preferably by using a protein A column or the like, and whether the purified antibody has coagulation inhibitory activity is examined by measuring aPTT, dRVVT or XCT.

The measurement is performed by using, for example, PTT-LA (Diagnostica Stago) for aPTT, dRVVT Reagent 1 (Gradipore LA, MBL) for dRVVT, or kaolin (Boehringer) for KCT. When PTT-LA and dRVVT are used, coagulation time is measured according to their attached instructions. Further, as for KCT, 50 µl each of a standard or sample and the kaolin reagent are mixed, and incubated at 37° C. for 2 minutes and then 50 µl of 0.025 M $CaCl_2$ is added and the coagulation time is measured.

Then, the obtained antibody is confirmed to dose-dependently prolong the coagulation time.

The 231D antibody, which is an embodiment of the present invention, can be obtained from 231D cells. The 231D cells were deposited at the International Patent Organism Depositary, National Institute of Advanced Industrial Science and Technology (formerly National Institute of Bioscience and Human-Technology, Agency of Industrial science and Technology, Ministry of International Trade and Industry, Postal address; Tsukuba Central 6, 1-1-1 Higashi, Tsukuba, Ibaraki, 305-8566 Japan) on Mar. 9, 2001 and given an accession number of FERM P-18247. Then, the deposition was converted to an international deposition under the provisions of the Budapest Treaty on Mar. 5, 2002 and given an accession number of FERM BP-7936.

The antibody of the present invention can be used as a standard in LA measurement. Accordingly, the present invention provides an LA measurement method using the antibody of the present invention as a standard.

The LA measurement method of the present invention is a method for measuring inhibitory activity of test plasma on blood coagulation reactions, which comprises the steps of:

(1) measuring inhibitory activity of the test plasma on the blood coagulation reactions and inhibitory activity of the antibody of the present invention on the blood coagulation reaction; and (2) comparing the inhibitory activity of the test plasma with the inhibitory activity of the antibody of the present invention.

The method for measuring the inhibitory activity on blood coagulation reactions is not particularly limited. The inhibitory activity can be measured by adding a substance of which inhibitory activity is to be measured to a reaction mixture used for measuring blood coagulation reactions to allow blood coagulation reactions and measuring influence of the substance on the blood coagulation reactions.

The method for measuring the inhibitory activity on blood coagulation reactions is preferably measurement of prolongation of activated partial thromboplastin time, measurement of prolongation of kaolin clotting time, measurement of prolongation of dilute Russell's viper venom time, or a combination thereof.

When the inhibitory activity on blood coagulation reactions is measured by measuring the prolongation of coagulation time, the inhibitory activity can be compared by, for example, preparing standard samples containing the antibody of the present invention at various concentrations, plotting the coagulation times of the standard samples along the Y-axis and the concentrations of the antibody of the present invention along the X-axis to create a standard curve and determining an antibody concentration corresponding to the test plasma using the coagulation time of the test plasma based on the standard curve.

Further, lupus anticoagulant in the test plasma can be measured by determining the lupus anticoagulant amount using the inhibitory activity measured by the aforementioned method as an index.

Hereafter, the LA measurement method using mouse monoclonal aPS/PT as a standard will be described as a specific example. However, the scope of the present invention is not limited to this example.

Normal plasma is filtered through a 0.22-μm filter to remove platelets. To the plasma from which platelets are removed, the purified 231D antibody is added at suitable serial dilutions, for example, 2-fold dilutions from 50 to 1.3 μg/ml, and 0 μg/ml to obtain standard samples.

Similarly, patient's plasma is filtered through a 0.22-μm filter to remove platelets. The patient's plasma from which platelets are removed and the normal plasma from which platelets are similarly removed are mixed at a suitable ratio, for example, patient's plasma:normal plasma=20:80 (volume ratio) to obtain test plasma.

The coagulation times of the standard samples and the test plasma are measured. As the reagent, for example, PTT-LA (Diagnostica Stago) is used for aPTT, dRVVT Reagent 1 (Gradipore LA, MBL) is used for dRVVT, or kaolin (Boehringer) is used for KCT. When PTT-LA or dRW T is used, the coagulation time is measured according to their attached instructions. As for KCT, 50 μl each of the standard or sample and the kaolin reagent are mixed, and incubated at 37° C. for 2 minutes and then 50 μl of 0.025 M $CaCl_2$ is added, and the coagulation time is measured.

For each reagent, a standard curve is created by plotting the coagulation times of the standard samples along the Y-axis and the concentrations of the 231D antibody along the X-axis. From the coagulation time of the test plasma, the concentration (μg/ml) of the 231D antibody corresponding to the anti-coagulation activity of the test plasma is read from the standard curve, and the value is considered as ACU (Anticoagulant Unit) of the test plasma. Further, ACUs of several tens of normal subjects are measured by using each reagent to determine a reference value as mean +2SD.

A test serum showing ACU higher than the reference value is determined as LA positive.

The present invention further provides a reagent for measuring lupus anticoagulant, which includes the antibody of the present invention as a constitutive reagent.

The reagent of the present invention may have the same constitution as conventional lupus anticoagulant measurement reagents except that the antibody of the present invention used as a standard is included. The antibody of the present invention may be combined with a carrier (buffer or the like) acceptable as a reagent and provided as a composition.

EXAMPLES

The present invention will be explained more specifically with reference to the following examples. However, the scope of the present invention is not limited to these examples.

Example 1

Preparation of Mouse Monoclonal aPS/PT (1) Preparation of Hybridoma

A Balb/c mouse was immunized with 50 μg/mouse of purified human prothrombin (Enzyme Research) once together with Freund's complete adjuvant, and further twice with Freund's incomplete adjuvant after 14 and 28 days. Elevation of the titer of antibodies directed to human prothrombin was confirmed, and 42 days after the final immunization, spleen was removed. The spleen was minced and passed through a mesh to separate lymphocytes.

The isolated lymphocytes and myeloma P3U1 cells were mixed at a ratio of 5:1 to 10:1, suspended in RPMI-1640 medium and centrifuged. The cell aggregation was loosened, and 1 ml of 50% PEG solution (Boehringer) warmed at 37° C. beforehand was gradually added over 2 minutes. Subsequently, 20 ml of RPMI-1640 medium warmed at 37° C. beforehand was gradually added over 3 minutes. The mixture was centrifuged at 1000 rpm for 5 minutes and left for 5 minutes to allow cell fusion. Supernatant was removed, and then lymphocyte cells were suspended in 10% FCS/RPMI-1640 medium at $1 \times 10^6$ cells/ml and introduced into each well of twenty 96-well plates in a volume of 100 μl per well. On the following day, 100 μl/well of 10% FCS/2× HAT (Lifetech)/RPMI-1640 medium was added to start selection of hybridoma Following 12 days after the start of the culture, culture supernatant was collected and subjected to an assay of antibody.

(2) Selection of Clone Producing Antibody Reacting with PS/PT

Phosphatidylserine (Sigma) was dissolved in a methanol/chloroform solvent at 50 μg/ml, and 30 μl of the solution was added to an ELISA plate (Sumitomo Bakelite). Then, the solvent was evaporated, and 150 μl of albumin solution (10 mg/ml BSA (fatty acid free, Sigma), 5 mM $CaCl_2$, 150 mM NaCl, 10 mM Tris-HCl, pH 7-5) was added to perform blocking. After washing, 50 μl of prothrombin solution (10 μg/ml human prothrombin (Diagonostica Stago), 10 mg/ml ESA, 5 mM $CaCl_2$, 150 mM NaCl, 10 mM Tris-HCl, pH 7.5) was added to form PS/PT complexes on the ELISA plate. Further, as a control, the albumin solution without human prothrombin was added to a well.

The ELISA plate was washed, and then 50 μl of the hybridoma culture supernatant diluted 20-fold to 1000-fold was added to the plate and reacted with the PS/PT complex formed on the ELISA plate. After washing, the reaction product was further reacted with an anti-mouse Ig antibody labeled with alkaline phosphatase. After washing, a substrate of alkaline phosphatase was added to develop the color. Each well was compared with the well to which the albumin solution was added, and a clone showing stronger color development in the wells to which the purified human prothrombin solution was added was selected as a clone producing antibodies that reacting with PS/PT.

(3) Selection of Clone Producing Antibody not Reacting with PT

80 μl of 10 μg/ml solution of purified human prothrombin dissolved in PBS was added to an ELISA plate. After washing, 0.5% gelatin solution was added to perform blocking.

The ELISA plate was washed, and then 50 μl of the culture supernatant of hybridoma selected in (2) diluted 20-fold to 1000-fold was added to the plate and reacted with PT on the ELISA plate. After washing, the reaction product was further reacted with an anti-mouse Ig antibody labeled with alkaline phosphatase. After washing, a substrate of alkaline phosphatase was added to develop the color, and a clone not developing the color was selected as a clone producing antibodies not reacting with PT.

As a clone producing an antibody reacting with PS/PT but not with PT, 231D cells (FERM BP-7936) were selected.

Hereinafter, the antibody produced by the 231D cells will be referred to the 231D antibody.

(4) Coagulation Inhibitory Activity of 231D Antibody

Normal plasma was filtered through a 0.22-µm filter to remove platelets. To the plasma from which platelets were removed, the purified 231D antibody was added at 50, 25, 12.5, 6.3, 3.1, 1.3 and 0 µg/ml. Coagulation time in each sample was measured.

As the reagents, PTT-LA (Diagnostica Stago), dRVVT Reagent 1 (Gradipore LA, MBL) and kaolin (Boehringer) were used. When PTT-LA or dRVVT was used, the coagulation time was measured according to their attached instructions. As for KCT, 50 µl each of the standard or a sample and the kaolin reagent were mixed, and incubated at 37° C. for 2 minutes, and then 50 µl of 0.025 M $CaCl_2$ was added, and the coagulation time was measured.

FIG. 1 shows a typical relationship between the 231D antibody amount and the coagulation time obtained by using aPPT. The 231D antibody showed dose-dependent activity for prolonging the coagulation time in each coagulation system. This result suggested that the 231D antibody could be used as a standard of the LA measurement.

Example 2

Measurement of LA Using 231D Antibody as Standard (1) Measurement Method for LA

Based on the results of Example 1, (4), semi-quantitative measurement was performed considering that anti-coagulation activity of the test plasma corresponding to 1 µg/ml of the 231D antibody as 1.0 ACU (Anticoagulant Unit) as determined from the standard curve created by the serial dilution of the 231D antibody. Specifically, the measurement was performed as follows.

Normal plasma was filtered through a 0.22-µm filter to remove platelets. To the plasma from which platelets were removed, the purified 231D antibody was added at 50, 25, 12.5, 6.3, 3.1, 1.3 and 0 µg/ml to obtain standard samples. Patient's plasma was similarly filtered through a 0.22-µm filter to remove platelets, and the patient's plasma from which platelets were removed and the normal plasma from which platelets were similarly removed were mixed at a ratio of patient's plasma:normal plasma=20:80 (volume ratio) to obtain test plasma.

The coagulation time of the standard samples and the test plasma was measured. As reagents, PTT-LA (Diagnostica Stago), dRVVT Reagent 1 (Gradipore LA, MBL) and kaolin (Boehringer) were used. When PTT-LA or dRVVT was used, the coagulation time was measured according to their attached instructions. As for KCT, 50 µl each of the standard or a sample and the kaolin reagent were mixed, and incubated at 37° C. for 2 minutes, and then 50 µl of 0.025 M $CaCl_2$ was added, and the coagulation time was measured.

For each reagent, a standard curve was created by plotting the coagulation times of the standard samples along the Y-axis and the concentrations of the 231D antibody along the X-axis. The concentration (µg/ml) of the 231D antibody corresponding to the anti-coagulation activity of the test plasma was read from the standard curve using the coagulation time of the test plasma, and the value was represented as ACU of the test plasma. Further, ACUs of several tens of normal subjects were measured by using each reagent to determine a reference value (mean+2SD).

(2) LA Measurement in APS Patient

LA was measured in total 163 autoimmune disease patients consisting of 47 patients with arterial or venous thrombosis or abortion (APS group, abbreviated as T) and 116 patients without thrombosis or abortion (non-APS group, abbreviated as non-T).

Figure 2:
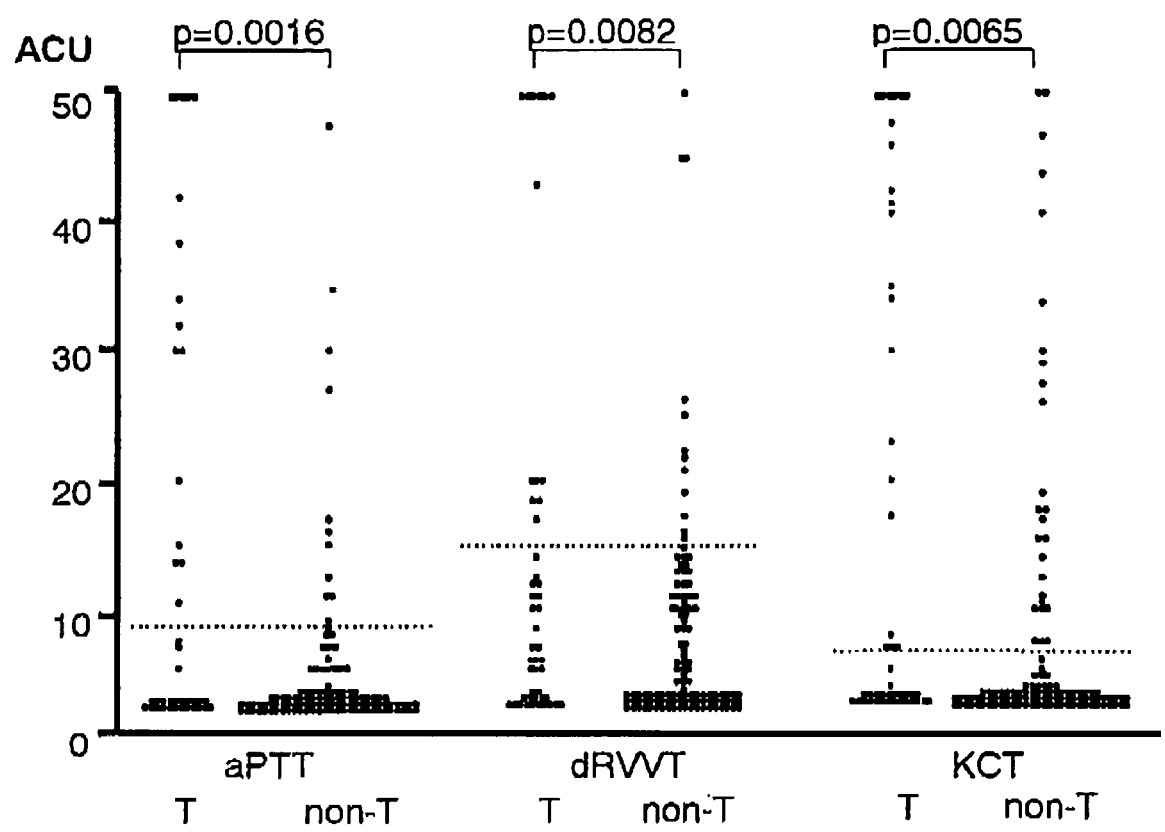
FIG. 2 shows distributions of AcU in the APS group and the non-APS group measured by using the 231D antibody as a standard. In the figure, dotted lines represent a reference value (mean of 30 normal subjects +2SD) of ACU.

When aPTT was solely used, ACU exceeded the reference value (mean of 30 normal subjects +2SD) in 17/47 (36%) for T and 12/116 (10%) for non-T. When dRVVT was solely used, ACU exceeded the reference value in 13/47 (28%) for T and 13/116 (11%) for non-T. When KCT was solely used, ACU exceeded the reference value in 21/47 (45%) for T and 25/116 (22%) for non-T (FIG. 2).

When aPTT, dRVVT and KCT were used in combination, ACU exceeded the reference value (mean of 30 normal subjects+2 SD) for any of these in 22 out of 47 patients for T (APS group). For non-T (non-APS group), ACU exceeded the reference value in 31 of 116 patients. That is, ACU exceeded the reference value in significantly more patients with APS.

(3) Influence of Warfarin on LA Measurement

It is known that the Gradipore reagent currently used for LA measurements provides false positive results in patients using warfarin. Accordingly, influence of warfarin on the LA measurement method using the 231D antibody as a standard was examined.

As a result, no particular influence was observed even when plasma of patients to which warfarin was administered was used (Table 1).

TABLE 1

|  |  | aPTT (ACU) | dRVVT (ACU) | KCT (ACU) |
|---|---|---|---|---|
| LA positive | 1 | 30 | 20 | 30 |
|  | 2 | >50 | >50 | >50 |
|  | 3 | 35 | 17 | 34 |
|  | 4 | 48 | >50 | >50 |
|  | 5 | 30 | >50 | >50 |
|  | 6 | 15 | 14 | 41 |
| Warfarin used | 7 | <3.1 | 14 | 3.3 |
|  | 8 | <3.1 | 12 | <3.1 |
|  | 9 | <3.1 | 3.5 | <3.1 |
|  | 10 | <3.1 | 3.5 | <3.1 |
|  | 11 | <3.1 | <3.1 | <3.1 |
| LA positive and warfarin used | 12 | >50 | 43 | >50 |
|  | 13 | >50 | 36 | 38 |
|  | 14 | >50 | >50 | >50 |
|  | 15 | 38 | 14 | 48 |

The above results revealed that, by using the 231D antibody, semi-quantitative measurement of LA was enabled, and thus LA could be more precisely determined.

INDUSTRIAL APPLICABILITY

Because the monoclonal antibody serving as a standard of LA is provided, by using the monoclonal antibody as a standard, it becomes possible to perform LA measurements, which have resulted in significant differences among institutions, with good precision even as semi-quantitative measurement.

What is claimed is:

1. An antibody produced by 231D cells (FERM BP-7936).
2. A method for comparing an inhibitory activity of plasma from a lupus patient with the inhibitory activity of a standard antibody on a blood coagulation reaction, comprising the steps of:

(1) measuring the inhibitory activity of the plasma on the blood coagulation reaction;
(2) measuring the inhibitory activity of the antibody as defined in claim 1 on the blood coagulation reaction, and
(3) comparing the inhibitory activity of the plasma with the inhibitory activity of the antibody.

3. A method for determining a lupus anticoagulant level in plasma from a lupus patient, comprising the steps of:
(1) measuring the inhibitory activity of the lupus patient's plasma on a blood coagulation reaction;
(2) measuring the inhibitory activity of the antibody as defined in claim 1 on the blood coagulation reaction, and
(3) comparing the inhibitory activity of the lupus patient's plasma with the inhibitory activity of the antibody to express the inhibitory activity of the lupus patient's plasma as a level of the antibody; and
(4) determining a lupus anticoagulant level by using the level of the antibody as an index.

4. The method according to claim 2, wherein the method for measuring the inhibitory activity on blood coagulation reactions is selected from the group consisting of measurement of prolongation of activated partial thromboplastin time, measurement of prolongation of kaolin clotting time, and measurement of prolongation of dilute Russell's viper venom time, or a combination thereof.

5. A reagent for measuring lupus anticoagulant, which comprises the monoclonal antibody as defined in claim 1 and a carrier.

* * * * *